(12) United States Patent
Nakai et al.

(10) Patent No.: US 9,408,803 B2
(45) Date of Patent: Aug. 9, 2016

(54) COMPOSITIONS CONTAINING LIGNAN-CLASS COMPOUNDS

(75) Inventors: Masaaki Nakai, Mishima-gun (JP); Yukihiro Aoshima, Mishima-gun (JP); Shuji Endo, Mishima-gun (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 0 days.

(21) Appl. No.: 12/295,078

(22) PCT Filed: Mar. 14, 2007

(86) PCT No.: PCT/JP2007/055113
§ 371 (c)(1),
(2), (4) Date: Sep. 29, 2008

(87) PCT Pub. No.: WO2007/114013
PCT Pub. Date: Oct. 11, 2007

(65) Prior Publication Data
US 2009/0247625 A1  Oct. 1, 2009

(30) Foreign Application Priority Data
Mar. 31, 2006 (JP) .................. 2006-097871

(51) Int. Cl.
A61K 31/36  (2006.01)
A61K 9/08  (2006.01)
A61K 9/48  (2006.01)
A61K 47/14  (2006.01)

(52) U.S. Cl.
CPC .................. *A61K 9/08* (2013.01); *A61K 9/4858* (2013.01); *A61K 31/36* (2013.01); *A61K 47/14* (2013.01)

(58) Field of Classification Search
CPC ...... A61K 9/4858; A61K 31/36; A61K 47/14
See application file for complete search history.

(56) References Cited

U.S. PATENT DOCUMENTS

| | | | | |
|---|---|---|---|---|
| 4,744,988 A * | 5/1988 | Brox | ........................... | 424/456 |
| 5,180,588 A | 1/1993 | Shinmen et al. | | |
| 5,211,953 A | 5/1993 | Shinmen et al. | | |
| 6,596,762 B2 * | 7/2003 | Sokol | ........................... | 514/458 |
| 2005/0095233 A1 * | 5/2005 | McCleary et al. | ........... | 424/94.1 |
| 2005/0147598 A1 | 7/2005 | Ueda et al. | | |
| 2005/0214361 A1 | 9/2005 | Mizutani et al. | | |
| 2006/0058376 A1 | 3/2006 | Moritani | | |
| 2006/0247310 A1 | 11/2006 | Shinohara et al. | | |
| 2007/0208077 A1 | 9/2007 | Ono | | |
| 2009/0156838 A1 | 6/2009 | Aoshima | | |
| 2009/0163583 A1 | 6/2009 | Aoshima et al. | | |
| 2009/0202643 A1 | 8/2009 | Yamada | | |

FOREIGN PATENT DOCUMENTS

| | | |
|---|---|---|
| EP | 387000 | 9/1990 |
| EP | 0 409 654 | 1/1991 |
| EP | 3-27319 | 2/1991 |
| EP | 4-9331 | 1/1992 |
| EP | 0 488 513 | 6/1992 |
| EP | 4 159221 | 6/1992 |
| EP | 0 729 753 | 9/1996 |
| EP | 8-268887 | 10/1996 |
| EP | 0 782 827 A1 | 7/1997 |
| EP | 1 930 333 A1 | 6/2008 |
| EP | 1 950 214 A1 | 7/2008 |
| GB | 1 432 784 | 4/1976 |
| JP | 49-71127 A | 7/1974 |
| JP | 54-92616 A | 7/1979 |
| JP | 59-013717 A | 1/1984 |
| JP | 3-53866 | 3/1991 |
| JP | 5-51388 | 3/1993 |
| JP | 05-163143 | 6/1993 |
| JP | 5178763 A | 7/1993 |
| JP | H06-009381 | 1/1994 |
| JP | 6-227977 | 8/1994 |
| JP | 10 120695 | 5/1998 |
| JP | 11-269456 | 10/1999 |
| JP | 2001-139579 | 5/2001 |
| JP | 4-261120 | 9/2002 |
| JP | 2006-280276 A | 10/2006 |
| JP | 2006-306864 | 11/2006 |
| JP | 2006-306864 A | 11/2006 |
| WO | WO 97/01968 | 1/1997 |
| WO | WO-03/062182 A1 | 7/2003 |
| WO | WO-03/094897 A1 | 11/2003 |
| WO | WO 2004/064830 A1 | 8/2004 |
| WO | WO 2004/105749 A1 | 12/2004 |
| WO | WO 2005/095414 A1 | 10/2005 |
| WO | WO 2006/016682 A1 | 2/2006 |
| WO | WO 2006/070856 | 7/2006 |
| WO | WO 2006/106926 A1 | 10/2006 |

OTHER PUBLICATIONS

International Preliminary Report on Patentability dated Oct. 21, 2008 in PCT/JP2007/055113.
Extended European Search Report dated Sep. 14, 2009 issued in European Application No. 07 738 583.9.
Supplementary European Search Report mailed Nov. 4, 2010, in European Application No. EP 06 79 8461.

(Continued)

*Primary Examiner* — Dennis Heyer
(74) *Attorney, Agent, or Firm* — Drinker Biddle & Reath LLP

(57) ABSTRACT

An object of the invention is to provide compositions containing lignan-class compounds as dissolved at high concentrations. The compositions having lignan-class compounds such as sesamin and episesamin dissolved in solvent oils or fats that contain triglycerides of middle-chain fatty acids having 8-12 carbon atoms, preferably triglycerides of caprylic acid and/or capric acid and/or lauric acid can contain the lignan-class compounds stably at higher concentrations than when other solvents are used and, hence, have high enough value as foods and pharmaceuticals.

32 Claims, No Drawings

(56) References Cited

OTHER PUBLICATIONS

Biswanath DAS et al., "Clay Catalysed Convenient Isomerization of Natural Furofuran Lignans Under Microwave Irradiation", Synthetic Communications, 2000, pp. 4001-4006, vol. 30, No. 22, Published by Marcel Dekker, Inc.

Y. Fukuda et al., "Contribution of Lignan Analogues to Antioxidative Activity of Refined Unroasted Sesame Seed Oil", J. Am. Oil Chem. Soc., Aug. 1986, pp. 1027-1031, vol. 63, No. 8.

International Search Report dated Nov. 28, 2006 for PCT/JP2006/319493 filed Sep. 29, 2006.

Namiki et al., "Goma—Sono Kagaku to Kinousei", Maruzen Planet Co., Ltd. (1998) p. 47, lines 3-4; and p. 51, lines 12-16 (partial translation).

Shimizu, Sakayu et al., "Production of Dihomo-γ-linolenic Acid by Mortierella alpina 1S-4", JAOCS, vol. 66, No. 2 (Feb. 1989) pp. 237-241.

Shimizu, Sakayu et al., "Sesamin Is a Potent and Specific Inhibitor of Δ5 Desaturase in Polyunsaturated Fatty Acid Biosynthesis", LIPIDS, vol. 26, No. 7 (1991), pp. 512-516.

Umeda-Sawada, Rumi et al., The Metabolism and Distribution of Sesame Lignans (sesamin and episesamin) in Rats, LIPIDS, vol. 34, No. 6 (1999), pp. 633-637.

Kushiro, Masayo et al., "Comparative Effect of Sesamin and Episesamin on the Activity and Gene Expression of Enzymes in Fatty Acid Oxidation and Synthesis in Rat Liver", Journal of Nutritional Biochemistry 13 (2002) pp. 289-295.

Office Action mailed Sep. 14, 2010 in U.S. Appl. No. 11/992,196.

Office Action mailed Aug. 5, 2010 in U.S. Appl. No. 11/992,196.

* cited by examiner

COMPOSITIONS CONTAINING LIGNAN-CLASS COMPOUNDS

CROSS REFERENCE TO RELATED APPLICATIONS

This application is the National Stage of International Application No. PCT/JP2007/055113 filed Mar. 14, 2007, and claims benefit of Japanese Application No. 97871/2006 filed Mar. 31, 2006, both of which are herein incorporated by reference in their entirety.

TECHNICAL FIELD

This invention relates to compositions containing lignan-class compounds. More particularly, this invention relates to compositions comprising sesamin and/or episesamin and glycerides of middle-chain fatty acid having 8-12 carbon atoms.

BACKGROUND ART

Lignan-like compounds are known to be used in a variety of applications. For example, U.S. Pat. No. 4,427,694 discloses the effectiveness of sesamin in alleviating the symptoms of alcohol intoxication and/or alcohol or tobacco withdrawal, and JP 2-138120 A discloses the effectiveness of sesaminol and episesaminol in the treatment and prevention of allergosis such as bronchial asthma. The assignees of the subject application also confirmed various physiological actions of lignan-class compounds and, to date, they have shown such effects as the blood cholesterol lowering action (Japanese Patent No. 3001589), the action of inhibiting $\Delta 5$-unsauration enzymes (Japanese Patent No. 3070611), the action of improving hepatic functions (Japanese Patent No. 3075358), the cholesterol depressing action (Japanese Patent 3075360), the action of preventing sickness from drinking (Japanese Patent No. 3124062), the action of inhibiting the metabolism of cholesterol and bile acid, as well as lowering cholesterol (Japanese Patent No. 3283274), the carcinogenesis suppressing action (Japanese Patent No. 3183664), the breast cancer suppressing action (JP 05-043458 A), as well as the action of suppressing the generation of lipid peroxides (JP 05-051388 A), and the action of scavenging active oxygen (JP 06-227977 A).

Speaking of fat-soluble substances, they are generally low in bodily absorption after ingestion by humans or animals. Hence, there have been proposed methods for enhancing the absorption of fat-soluble substances. Take, for example, the fat-soluble ubidecarenon and there has been disclosed a method that enhances its absorption by dissolving it in edible natural fats or oils or triglycerides of middle-chain fatty acids to form liquids (JP 54-92616 A).

Patent Document 1: U.S. Pat. No. 4,427,694
Patent Document 2: JP 2-138120 A
Patent Document 3: Japanese Patent No. 3001589
Patent Document 4: Japanese Patent No. 3070611
Patent Document 5: Japanese Patent No. 3075358
Patent Document 6: Japanese Patent No. 3075360
Patent Document 7: Japanese Patent No. 3124062
Patent Document 8: Japanese Patent No. 3283274
Patent Document 9: JP 04-159221 A (Japanese Patent No. 3183664)
Patent Document 10: JP 05-043458 A
Patent Document 11: JP 05-051388 A
Patent Document 12: JP 06-227977 A
Patent Document 13: JP 54-92616 A

DISCLOSURE OF THE INVENTION

Problems to be Solved by the Invention

The present inventors performed absorption experiments in rats using two fat-soluble substances, sesamin and episesamin, both for the case of a suspension where they were dispersed in water and for the case of a solution where they were dissolved in fat or oil (wheat germ oil), and confirmed that the latter was significantly superior in bodily absorption. It may well be said that a preferred mode of ingesting sesamin and/or episesamin is by dissolving them in fat or oil; however, sesamin and/or episesamin is only slightly soluble and has such low solubility in fat or oil (wheat germ oil) that not only is it difficult to incorporate them at high concentrations but, at the same time, even if they are incorporated at low concentrations, a crystal may precipitate during storage on account of their low storage stability. This crystal precipitation can potentially result in lowered absorbability, so considering the storage stability, there has been no alternative to incorporating them at concentrations considerably lower than their solubility in fat or oil (wheat germ oil). Under these circumstances, when one made an attempt to increase the dose of sesamin and/or episesamin that could be ingested at a time, the amount of the solvent fat or oil also had to be increased, inevitably resulting in an excessive calorie intake. In addition, the volume of the sesamin and/or episesamin containing composition that is prescribed becomes so large per unit dosage or their quantities to be ingested become so large that inconveniences in ingestion have occasionally occurred. In particular, in the case of formulating for oral administration, the preparation (e.g. capsule) becomes so big or the number of capsules to be ingested becomes so large that impediments to ingestion have occasionally occurred.

An object of the present invention is to provide compositions that allow fat-soluble substances, sesamin and/or episesamin, to be incorporated at high concentrations.

Means for Solving the Problems

As the result of the intensive studies they made in order to solve the aforementioned problems, the present inventors found that when triglycerides of middle-chain fatty acids having 8-12 carbon atoms were used as solvents, the solubility of sesamin and/or episesamin improved by a factor of about 2.5 to 5.5 over the case of wheat germ oil which was composed of long-chain fatty acids. And as the result of a further study, the present inventors found that sesamin and its isomer episesamin were different in solubility, episesamin being less soluble than the slightly soluble sesamin, and that the difference between the solubilities of sesamin and episesamin was great in the triglycerides of middle-chain fatty acids; the present invention has been accomplished on the basis of these findings.

Thus, the present invention relates to a composition containing sesamin and/or episesamin and a triglyceride of a middle-chain fatty acid having 8-12 carbon atoms, the sesamin and/or episesamin being dissolved in the middle-chain fatty acid triglyceride.

The present invention also relates to a food or beverage that contain the composition and which are preferably in the form of a capsule.

Effect of the Invention

The composition of the present invention contains sesamin and/or episesamin at much higher concentrations than have heretofore been possible and it has not only outstanding storage stability but also high safety. Since the composition of the present invention contains high concentrations of sesamin and/or episesamin, it can be ingested perorally as soft capsules and the like, with smaller quantities of capsules being ingested and with less oil being ingested as a solvent.

In addition, according to the present invention, capsules can be provided that contain at least 1.0 wt % of the slightly soluble episesamin (or an episesamin-rich composition) which has heretofore been unattainable.

Furthermore, according to the present invention, episesamin can be purified by making use of the difference in solubility between sesamin and episesamin in middle-chain fatty acid triglycerides.

BEST MODE FOR CARRYING OUT THE INVENTION

Lignan-Class Compounds

The sesamin and episesamin to be used in the present invention (which are hereinafter sometimes referred to as "lignan-class compounds") may be used either alone or in admixture.

The methods for obtaining the lignan-class compounds to be added to foods according to the present invention and an extract that contains the lignan-class compounds as a main component and which may also be added to foods according to the present invention, can be performed by the following procedures. First, there is described case where an extract that contains the lignan-class compounds as a main component is obtained from sesame oil; in this case, extracting and concentrating may be performed using a variety of organic solvents that are substantially immiscible with the sesame oil and which can extract and dissolve the lignan-class compounds. Examples of such organic solvents include acetone, methyl ethyl ketone, diethyl ketone, methanol, ethanol, and the like. In order to obtain an extract that contains the lignan-class compounds as a main component, one may, for example, mix sesame oil with any one of those solvents uniformly, allow the mixture to stand at low temperature, perform phase separation in accordance with a standard procedure such as centrifugation, and remove the solvent from the solvent fraction by evaporation. More specifically, sesame oil is dissolved in 2-10 volumes, preferably 6-8 volumes, of acetone and left to stand overnight at −80° C. As a result, the oil component forms a precipitate and from the filtrate obtained by filtration, the organic solvent is distilled off to yield an extract that contains the lignan-class compounds as a main component. Alternatively, sesame oil is mixed with hot methanol or hot ethanol, the mixture is allowed to stand at room temperature, and the solvent is removed from the solvent fraction by evaporation. More specifically, the sesame oil is mixed with 2-10 volumes, preferably 5-7 volumes, of hot methanol (≥50° C.) or hot ethanol ((≥50° C.) and extracted vigorously. Phase separation is performed by standing at room temperature or in accordance with a standard procedure such as centrifugation and the solvent is distilled off from the solvent fraction to yield an extract that contains the lignan-class compounds as a main component. Supercritical gas extraction can also be utilized. In order to obtain various lignan-class compounds from the extract, the extract may be treated in accordance with a standard procedure such as column chromatography, high-performance liquid chromatography, recrystallization, distillation, or liquid-liquid countercurrent partition chromatography, whereupon the desired compound is isolated. More specifically, using a reverse-phase column and methanol/water (60:40) as an eluant, the extract mentioned above is separated out by high-performance liquid chromatography and after the solvent is distilled off, the resulting crystal is recrystallized with ethanol to yield various lignan-class compounds such as sesamin, episesamin, sesaminol, episesaminol, etc. The sesame oil to be used may be a refined product or it may be a crude product obtained at any stage of the process of sesame oil production, except that it is prior to the decoloring step; if desired, sesame seeds or sesame oil cake (sesame seeds from with oil has been expressed to give a residual oil content of 8-10%) may be substituted. In this case, the sesame seeds or sesame oil cake may optionally be crushed and extracted by a standard procedure using any solvent, for example, one of the solvents described above in connection with the extraction from sesame oil. After separating the extraction residue, the solvent is distilled off from the liquid extract by, for example, evaporation, thus yielding the intended extract. From the thus purified forms of sesame seed extract, sesame oil cake extract or the extract of sesame oil in crude form, not only sesamin, episesamin, sesaminol and episesaminol but also various other lignan-class compounds, i.e., sesamolin, 2-(3,4-methylenedioxyphenyl)-6-(3-methoxy-4-hydroxyphenyl)-3,7-dioxabicyclo[3,3,0]octane, 2,6-bis-(3-methoxy-4-hydroxyphenyl)-3,7-dioxabicyclo[3,3,0]octane, or 2-(3,4-methylenedioxyphenyl)-6-(3-methoxy-4-hydroxyphenoxy)-3,7-dioxabicyclo[3,3,0]octane, can be obtained by similar techniques.

Note that the sesamin obtained from Asiasari Radix also has comparable effects to the sesamin obtained from sesame seeds and sesame oil and that these optically active forms are also included among the lignan-class compounds. In addition, lignan-class compounds can also be obtained from by-products to the process of sesame oil production. Note that the method of refining the lignan-class compounds and the method of obtaining the extract are by no means limited to those described above. In addition, the above-mentioned lignan-class compounds and lignan-class compound based extract are by no means limited to those obtained from sesame oil, sesame oil cake, and sesame seeds, and all natural products that contain the lignan-class compounds can also be employed. Examples of such natural products include Acanthopoanacis Cortex, *paulownia* tree, *ginkgo* bark, *Piper retrofractum*, Asiasari Radix, etc.

The following may be mentioned as methods for obtaining the lignan-class compounds by synthesis. For instance, sesamin and episesamin can be synthesized by the method of Beroza et al. (J. Am. Chem. Soc., 78, 1242 (1956)); in addition, pinoresinol can be synthesized by the method of Freundenberg et al. (Chem. Ber., 86, 1157 (1953)), and siringaresinol can be synthesized by the method of Freundenberg et al. (Chem. Ber., 88, 16 (1955)).

Furthermore, the lignan-class compounds can not only be used in the form of glycosides but they can also be incorporated, either alone or in suitable combinations, as ingredients of compositions.

Solvents (Middle-Chain Fatty Acid Glycerides)

In the present invention, the lignan-class compounds are dissolved in oils or fats that contain glycerides (comprising one or more of mono-, di- or triglycerides) of middle-chain fatty acids having 8-12 carbon atoms.

Except in a special case, the term "glycerides of middle-chain fatty acids having 8-12 carbon atoms" as used herein refers to mono-, di- or triglycerides that have fatty acids ester bonded to glycerol (which are sometimes referred to as mono-, di- or triacylglycerols) and in which at least one constituent fatty acid moiety derives from a middle-chain fatty acid having 8-12 carbon atoms. The carbon chain in the fatty acid may be straight-chained or branched.

Hereinafter, that part of the glyceride which derives from a middle-chain fatty acid may sometimes be referred to simply as a "middle-chain fatty acid."

The middle-chain fatty acid glyceride which serves as a solvent for the lignan-class compounds in the composition of the present invention may be either a mono-, di- or triglyceride or a mixture thereof, but triglycerides, in particular, triglycerides in which all constituent fatty acids are middle-chain fatty acids (hereinafter, these are sometimes referred to as "MCTs", such as tricaprylin) can be used with advantage.

In the present invention, the middle-chain fatty acids may be either saturated or unsaturated fatty acids but saturated fatty acids are preferred from the viewpoint of improving the stability of fatty acid glycerides against oxidation and the like.

Middle-chain fatty acids that are preferred in the present invention include, for example, caprylic acid, peralgonic acid, capric acid, undecylic acid, and lauric acid. In the case of forming a diglyceride or a triglyceride, these fatty acids may be composed of single species or they may be composed of two or more species.

Particularly preferred middle-chain fatty acid glycerides are triglycerides in which all constituent fatty acids are middle-chain fatty acids, and an example is a triglyceride in which the middle-chain fatty acid is at least one member selected from the group consisting of caprylic acid, capric acid, and lauric acid.

As middle-chain fatty acid triglycerides, those which are found as ingredients in vegetable fats or oils such as palm oil, coconut oil and babassu oil can be used; alternatively, artificially synthesized ones can also be used.

The fats or oils that serve as a solvent for dissolving the lignan-class compounds may be solely composed of middle-chain fatty acid glycerides or, so long as middle-chain fatty acid glycerides are contained in such amounts or incorporated at such ratios that they are effective for dissolving the lignan-class compounds stably, the fats or oils may be compositions that consist of the middle-chain fatty acid glycerides and other fatty acid glycerides. The ratios at which the middle-chain fatty acid glycerides are incorporated in the fats or oils may, for example, 5-100%, 10-100%, 25-100%, 50-100% or 75-100%, by weight of the total quantity of the fats or oils.

The middle-chain fatty acid glycerides have the advantages that they do not easily accumulate in the body and that they are not easily oxidized. In addition, the middle-chain fatty acid triglycerides are inherently contained in the fat content of dairy products, palm oil and the like and hence are ingredients that have a long proven record of use in meals.

Lignan-Class Compound Containing Compositions, as Well as Foods and Beverages

In order to produce the composition of the present invention, a lignan-class compound or compounds in powder form are added to a solubilizing agent (solvent) and mixed, preferably with agitation under heating so that they are fully dissolved. When a middle-chain fatty acid triglyceride is used as a solvent, the lignan-class compound or compounds will dissolve fully if the lignan-class compound or compounds and the solvent are incorporated at (weight) ratios of about 1:15 to about 1:100.

As used herein, the term "foods and beverages" include seasonings, nutraceutical products, health foods, foods for alimentary therapy, combination health foods, dietary supplements and beverages, as well as pharmaceuticals for oral administration. The foods and beverages according to the present invention can be formulated in either a solid form (e.g. crystals, capsules, tablets or powder), or a semi-solid form (e.g. gel or paste) or as a liquid form (e.g. mineral water, soft drink, fruit drink, sports drink, or alcoholic beverages); these foods and beverages preferably contain the lignan-class compound or compounds in solution, which is a state that permits easy absorption by the body, so the foods and beverages according to the present invention are preferably in the form of capsules (in particular, soft capsules), drinks, and the like.

The foods and beverages of the present invention can be produced by incorporating the compositions of the present invention using techniques known to skilled artisans. The foods and beverages of the present invention enable the lignan-class compounds to exhibit their desired effects in a consistent and efficient way.

The amounts of the lignan-class compounds to be incorporated in the foods and beverages of the present invention are not limited to any particular values and can appropriately be set by a skilled artisan with reference to a preferred daily intake of the lignan-class compound or compounds depending upon the form in which the food or beverage is ingested. Usually, the lignan-class compound or compounds are added such that at least 0.0001 wt %, especially at least 0.001 wt %, of them are contained in the foods or beverages of the present invention.

The compositions of the present invention may optionally contain any additives aside from the lignan-class compounds and the glycerides of middle-chain fatty acids having 8-12 carbon atoms. In addition, aside from the compositions of the present invention, the foods and beverages of the present invention may contain any ingredients that are used in ordinary foods and beverages. Examples of these additives and/or ingredients include vitamins such as vitamin E and vitamin C, sugars, vehicles, disintegrants, binders, lubricants, emulsifiers, isotonization agents, buffers, solvent promoters, preservatives, stabilizers, antioxidants, coloring agents, flavoring agents, scents, coagulants, pH adjusters, thickening agents, extract powders, galenicals, and inorganic salts.

Note that the compositions of the present invention for use in foods or beverages or the foods or beverages according to the present invention may have labels attached that state their specific uses (e.g. for supplementing nutrition, for maintaining health, and the like) and/or their specific usage (e.g., the amount of intake, the number of ingestions, the method of ingestion, and the like).

In recent years, the superior effects of episesamin began to be reported, such as episesamin markedly increasing the gene expression and enzymatic activity of β-oxidation enzymes in the liver as compared with sesamin (Kushiro, M. et al., J. Nutr. Biochem., 13, 289-295 (2002)). Therefore, the development of compositions containing episesamin as an active ingredient is anticipated. However, according to the study of the present inventors, it has been found that sesamin and episesamin have different solubilities, the latter being less soluble (see Example 1). Therefore, if a composition, supplement (capsule) that has episesamin as an active ingredient is to be produced using the conventionally found wheat germ oil or the like as a solubilizer, the problem of episesamin precipitation will occur during storage.

The present invention can be applied advantageously in preparing such capsules containing episesamin as an active ingredient. Specifically, heretofore unattainable capsules can be prepared that have episesamin added in such a way that at least 1.0 wt % of it is dissolved in the core composition (the contents other than the capsule shell).

In addition, the aforementioned difference in solubility between sesamin and episesamin tends to increase in MCTs (see Example 1). Therefore, MCTs can be utilized when one attempts to obtain an episesamin-rich composition from the mixture of sesamin and episesamin for such purposes as preparing the above-described composition containing episesamin as an active ingredient. Specifically, by dissolving the sesamin/episesamin mixture in MCTs and then performing recrystallization, episesamin can be purified to yield an episesamin-rich composition.

EXAMPLES

On the following pages, the present invention is further described in line with examples, to which the present invention is by no means limited.

Example 1

Solubility Test

1. Experimental Materials

Three samples were used and they included not only a mixture of sesamin and episesamin (sesamin:episesamin=51.1:48.2) but also sesamin and episesamin that were individually purified from the mixture. The wheat germ oil was a product of RIKEN VITAMIN CO., LTD.; the olive oil was a product of nakalai tesque; used as middle-chain fatty acids (MCTs) were ACTOR M-1 (a triglyceride of middle-chain fatty acid with C8:C10:C12=56:42:2) and ACTOR M-2 (a triglyceride of C8 middle-chain fatty acid), both being products of RIKEN VITAMIN CO., LTD. The diacylglycerol was a commercial fat or oil (Econa Cooking Oil of KAO CORPORATION, an edible oil containing about 80% diacylglycerol).

2. Experimental Method

Into test tubes, there were weighed 2 g of the respective fats or oils and various concentrations of the samples that increased from 0.5 to 10% (by weight) by an increment of 0.25%. Then, the test tubes were heated to 120° C. so that sesamin completely dissolved in the fats or oils. Thereafter, the test tubes were allowed to stand overnight at room temperature to examine whether crystals would be formed or not.

3. Results

As Table 1 shows, it unexpectedly turned out that the solubility of sesamin and/or episesamin was very low not only in the long-chain fatty acid triglycerides (LCTs) such as wheat germ oil and olive oil, but also in the diacylglycerol (DG), with their solubility being selectively high in the middle-chain fatty acid triglycerides (MCTs). From this result, it turned out that when one was attempting to produce supplements in the form of, say, soft capsules using sesamin and/or episesamin as an active ingredient, an increased amount of a lignan-class compound (say, sesamin) could be added per capsule by dissolving it in the MCT.

From the results in Table 1, it also turned out that there was a difference in solubility between sesamin and episesamin, the solubility in episesamin tending to be smaller. From these results, it turned out that when one was attempting to produce supplements in the form of, say, soft capsules using episesamin as an active ingredient, the technique of dissolving it in the aforementioned MCT was useful.

It should also be noted that the sesamin, episesamin and their mixture remained stable for at least 9 months at ordinary temperatures without precipitating.

TABLE 1

| Oil | Wheat germ oil | Oliver oil | MCT (ACTOR M-1) | MCT (Actor M-2) | DG |
|---|---|---|---|---|---|
| Mixture | 2.0 | 1.5 | 7.0 | 6.5 | 1.5 |
| Sesamin | 0.75 | 0.75 | 4.0 | 2.5 | 1.25 |
| Episesamin | 0.75 | 0.5 | 2.5 | 2.0 | 1.0 |

(dissolved in grams/100 g fat or oil)

Example 2

Production of Episesamin-Containing Composition

As fat or oil, MCT (ACTOR M-1 of RIKEN VITAMIN CO., LTD.) or wheat germ oil was used. Twenty grams of the fat or oil was weighed in an eggplant type flask of 50 ml in capacity; the flask was then charged with 4.0 g of a mixture of sesamin and episesamin (sesamin:episesamin=55:45) and heated in an oil bath at 120° C. with agitation until the mixture was completely dissolved. Thereafter, the mixture was slowly cooled by allowing it to stand in a 20° C. environment; when the liquid temperature reached 60° C., 4.0 mg of 100% episesamin seed crystals were charged and crystallization was performed for 30 minutes in a 20° C. environment. The liquor containing precipitating crystals was subjected to solid-liquid separation by suction filtration and the remaining solvent in the crystal mixture was washed off with 99.5% ethyl alcohol. The thus obtained crystal mixture was subjected to HPLC under the following conditions for analyzing the composition of sesamin and episesamin.

In addition, a mixture of sesamin and episesamin was heated to dissolve at 120° C. in the same manner as described above and, thereafter, following an activated clay treatment, recrystallization was effected in the same manner as described above to obtain a crystal mixture, which was analyzed for its composition. The activated clay treatment was such a treatment that 0.57 g of activated clay (GALLEON EARTH V2R manufactured by MIZUSAWA INDUSTRIAL CHEMICALS, LTD.) was added to the mixture of sesamin and episesamin that had been heated to dissolve in an oil bath and that following a 30-min treatment at 120° C., the waste clay was removed by filtration.

(HPLC Conditions)
Column: Inertsil ODS-3 (product of GL-SCIENCE) 4.6×150 mm
Column temperature: 40° C.
Mobile phase: methyl alcohol/water=7:3
Flow rate: 1 ml/min
Detector: UV 290 nm The episesamin content (purity) in the crystals obtained was 67.4% without the activated clay treatment and 94.0% with the activated clay treatment. Since the episesamin content before the recrystallization was 45%, it was found that episesamin could be purified by dissolving the sesamin/episesamin mixture in MCT and performing recrystallization.

Example 3

Capsule-1

Sesamin with the formulation indicated below (sesamin:episesamin~1:1) was dissolved in MCT under heating and thereafter cooled to prepare a sesamin-containing composition. This composition was filled into gelatin shells by the usual rotary process to prepare soft capsules each weighing 250 mg (with liquid contents weighing 210 mg).

| (Liquid contents) | |
|---|---|
| Sesamin | 10 mg |
| MCT | 200 mg |
| (Shell) | |
| Gelatin | 60.0% |
| Glycerin | 30.0% |

-continued

| | |
|---|---|
| Methyl paraoxybenzoate | 0.15% |
| Propyl paraoxybenzoate | 0.51% |
| Water | q.s. |

Example 4

Capsule-2

Two compositions were prepared (purified) as in Example 2 such that they contained episesamin at high concentrations (sesamin:episesamin=32.6:67.4, and 6.0:94.0); those compositions were used as lignan-class compounds. The lignan-class compounds with the formulation indicated below were dissolved in an oil or fat consisting of MCT:wheat germ oil=25:75 under heating and thereafter cooled to prepare lignan-class compound containing compositions. These compositions were filled into gelatin shells by the usual rotary process to prepare soft capsules each weighing 250 mg (with liquid contents weighing 200 mg). Both samples of soft capsules were free from the precipitation of crystals during storage.

| (Liquid contents) | |
|---|---|
| Lignan-class compounds | 3 mg |
| Vitamin E | 20 mg |
| Oil | 177 mg |
| (Shell) | |
| Gelatin | 60.0% |
| Glycerin | 30.0% |
| Methyl paraoxybenzoate | 0.15% |
| Propyl paraoxybenzoate | 0.51% |
| Water | q.s. |

The invention claimed is:

1. A composition consisting of:
a) sesamin and/or episesamin;
b) an oil or fat that contains a triglyceride of a middle-chain fatty acid having 8-12 carbon atoms, wherein a weight ratio of a total amount of sesamin and episesamin to a total amount of the triglyceride is about 1:40 to about 1:14.3; and
c) a vitamin, wherein the vitamin is selected from the group consisting of Vitamin E and Vitamin C,
wherein the composition has sesamin and/or episesamin dissolved therein.

2. The composition of claim 1, wherein the vitamin is Vitamin E.

3. The composition of claim 1, wherein the triglyceride of a middle-chain fatty acid comprises at least one middle-chain fatty acid selected from the group consisting of caprylic acid, capric acid, and lauric acid.

4. The composition of claim 1, wherein the triglyceride of a middle-chain fatty acid comprises at least one triglyceride in which all constituent fatty acids are middle-chain fatty acids (MCT).

5. The composition of claim 1, wherein the triglyceride of a middle-chain fatty acid consists of a triglyceride in which all constituent fatty acids are middle-chain fatty acids (MCT).

6. The composition of claim 5, wherein all of the fatty acids constituting the MCT are selected from the group consisting of caprylic acid, capric acid, and lauric acid.

7. A composition consisting of:
a) at least 1.0 wt % episesamin;
b) an oil or fat that contains a triglyceride of a middle-chain fatty acid having 8-12 carbon atoms, wherein a weight ratio of an amount of episesamin to a total amount of the triglyceride is about 1:50 to about 1:40; and
c) a vitamin, wherein the vitamin is selected from the group consisting of Vitamin E and Vitamin C,
wherein the composition has episesamin dissolved therein.

8. The composition of claim 7, wherein the vitamin is Vitamin E.

9. The composition of claim 7, wherein the triglyceride of a middle-chain fatty acid comprises at least one middle-chain fatty acid selected from the group consisting of caprylic acid, capric acid, and lauric acid.

10. The composition of claim 7, wherein the triglyceride of a middle-chain fatty acid comprises at least one triglyceride in which all constituent fatty acids are middle-chain fatty acids (MCT).

11. The composition of claim 7, wherein the triglyceride of a middle-chain fatty acid consists of a triglyceride in which all constituent fatty acids are middle-chain fatty acids (MCT).

12. The composition of claim 11, wherein ail of the fatty acids constituting the MCT are selected from the group consisting of caprylic acid, capric acid, and lauric acid.

13. A composition consisting of:
sesamin and/or episesamin;
b) an oil or fat that contains a triglyceride of a middle-chain fatty acid having 8-12 carbon atoms, wherein the triglyceride of a middle-chain fatty acid comprises at least one triglyceride in which all constituent fatty acids are middle-chain fatty acids (MCT), and wherein a total amount of the MCT(s) is 25-100% by weight of a total amount of the oil or fat; and
c) a vitamin, wherein the vitamin is selected from the group consisting of Vitamin E and Vitamin C,
wherein the composition has sesamin and/or episesamin dissolved therein.

14. The composition of claim 13, wherein the vitamin is Vitamin E.

15. The composition of claim 13, wherein the triglyceride of a middle-chain fatty acid consists of a triglyceride in which all constituent fatty acids are middle-chain fatty acids (MCT).

16. The composition of claim 15, wherein all of the fatty acids constituting the MCT are selected from the group consisting of caprylic acid, capric acid, and lauric acid.

17. A composition consisting of:
a) sesamin and/or episesamin;
b) an oil or fat that contains a triglyceride of a middle-chain fatty acid having 8-12 carbon atoms, wherein a weight ratio of a total amount of sesamin and episesamin to a total amount of the triglyceride is about 1:40 to about 1:14.3;
c) a vitamin, wherein the vitamin is selected from the group consisting of Vitamin E and Vitamin C; and
d) an additive selected from the group consisting of a sugar, a vehicle, a disintegrant, a binder, a lubricant, an emulsifier, an isotonization agent, a buffer, a solvent promoter, a preservative, a stabilizer, an antioxidant, a coloring agent, a flavoring agent, a scent, a coagulant, a pH adjuster, a thickening agent, an extract powder, a galenical, and an inorganic salt,
wherein the composition has sesamin and/or episesamin dissolved therein.

18. The composition of claim 17, wherein the vitamin is Vitamin E.

19. The composition of claim 17, wherein the triglyceride of a middle-chain fatty acid comprises at least one middle-chain fatty acid selected from the group consisting of caprylic acid, capric acid, and lauric acid.

20. The composition of claim 17, wherein the triglyceride of a middle-chain fatty acid comprises at least one triglyceride in which all constituent fatty acids are middle-chain fatty acids (MCT).

21. The composition of claim 17, wherein the triglyceride of a middle-chain fatty acid consists of a triglyceride in which all constituent fatty acids are middle-chain fatty acids (MCT).

22. The composition of claim 21, wherein all of the fatty acids constituting the MCT are selected from the group consisting of caprylic acid, capric acid, and lauric acid.

23. A composition consisting of:
 a) at least 1.0 wt % episesamin;
 b) an oil or fat that contains a triglyceride of a middle-chain fatty acid having 8-12 carbon atoms, wherein a weight ratio of an amount of episesamin to a total amount of the triglyceride is about 1:50 to about 1:40;
 c) a vitamin, wherein the vitamin is selected from the group consisting of Vitamin E and Vitamin C; and
 d) an additive selected from the group consisting of a sugar, a vehicle, a disintegrant, a binder, a lubricant, an emulsifier, an isotonization agent, a buffer, a solvent promoter, a preservative, a stabilizer, an antioxidant, a coloring agent, a flavoring agent, a scent, a coagulant, a pH adjuster, a thickening agent, an extract powder, a galenical, and an inorganic salt,
wherein the composition has episesamin dissolved therein.

24. The composition of claim 23, wherein the vitamin is Vitamin E.

25. The composition of claim 23, wherein the triglyceride of a middle chain fatty acid comprises at least one middle-chain fatty acid selected from the group consisting of caprylic acid, capric acid, and lauric acid.

26. The composition of claim 23, wherein the triglyceride of a middle-chain fatty acid comprises at least one triglyceride in which all constituent fatty acids are middle-chain fatty acids (MCT).

27. The composition of claim 23, wherein the triglyceride of a middle-chain fatty acid consists of a triglyceride in which all constituent fatty acids are middle-chain fatty acids (MCT).

28. The composition of claim 27, wherein all of the fatty acids constituting the MCT are selected from the group consisting of caprylic acid, capric acid, and lauric acid.

29. A composition consisting of;
 a) sesamin and/or episesamin;
 b) an oil or fat that contains a triglyceride of a middle-chain fatty acid having 8-12 carbon atoms, wherein the triglyceride of a middle-chain fatty acid comprises at least one triglyceride in which all constituent fatty acids are middle-chain fatty acids (MCT), and wherein a total amount of the MCT(s) is 25100% by weight of a total amount of the oil or fat;
 c) a vitamin, wherein the vitamin is selected from the group consisting of Vitamin E and Vitamin C; and
 d) an additive selected from the group consisting of a sugar, a vehicle, a disintegrant, a binder, a lubricant, an emulsifier, an isotonization agent, a buffer, a solvent promoter, a preservative, a stabilizer, an antioxidant, a coloring agent, a flavoring agent, a scent, a coagulant, a pH adjuster, a thickening agent, an extract powder, a galenical, and an inorganic salt,
wherein the composition has sesamin and/or episesamin dissolved therein.

30. The composition of claim 29, wherein the vitamin is Vitamin E.

31. The composition of claim 29, wherein the triglyceride of a middle-chain fatty acid consists of a triglyceride in which all constituent fatty acids are middle-chain fatty acids (MCT).

32. The composition of claim 31, wherein all of the fatty acids constituting the MCT are selected from the group consisting of caprylic acid, capric acid, and lauric acid.

\* \* \* \* \*